(12) United States Patent
Clomburg, Jr. et al.

(10) Patent No.: US 8,461,216 B2
(45) Date of Patent: Jun. 11, 2013

(54) PROCESS FOR THE CO-PRODUCTION OF SUPERHEATED STEAM AND METHANE

(75) Inventors: Lloyd Anthony Clomburg, Jr., Houston, TX (US); Anand Nilekar, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/388,311

(22) PCT Filed: Aug. 2, 2010

(86) PCT No.: PCT/US2010/044065
§ 371 (c)(1),
(2), (4) Date: Mar. 1, 2012

(87) PCT Pub. No.: WO2011/017243
PCT Pub. Date: Feb. 10, 2011

(65) Prior Publication Data
US 2012/0148481 A1   Jun. 14, 2012

Related U.S. Application Data

(60) Provisional application No. 61/230,777, filed on Aug. 3, 2009.

(51) Int. Cl.
*C07C 27/00* (2006.01)
(52) U.S. Cl.
USPC .................... 518/700; 702/703; 702/704
(58) Field of Classification Search
USPC .............................................. 518/700–704
See application file for complete search history.

(56) References Cited

U.S. PATENT DOCUMENTS

| | | | |
|---|---|---|---|
| 3,128,163 A | 4/1964 | Weittenhiller et al. | |
| 3,666,682 A | 5/1972 | Muenger | |
| 3,904,389 A | 9/1975 | Banquy | |
| 3,928,001 A | 12/1975 | Child et al. | |
| 3,970,435 A | 7/1976 | Schultz et al. | |
| 4,017,274 A | 4/1977 | Galstaun | |
| 4,046,523 A | 9/1977 | Kalina et al. | 48/197 R |
| 4,134,908 A | 1/1979 | Steiner et al. | 260/449.6 |
| 4,208,191 A | 6/1980 | Sze | |
| 4,235,044 A | 11/1980 | Cheung | |
| 4,298,694 A | 11/1981 | Skov | |
| 4,431,751 A | 2/1984 | Hohlein et al. | 518/706 |
| 4,839,391 A | 6/1989 | Range et al. | 518/712 |
| 6,755,980 B1 | 6/2004 | Van Den Born et al. | 210/767 |
| 2002/0004533 A1 | 1/2002 | Wallace et al. | |
| 2002/0055545 A1 | 5/2002 | Sheppard et al. | |
| 2006/0260191 A1 | 11/2006 | Van Den Berg et al. | 48/197 |
| 2007/0011945 A1 | 1/2007 | Grootveld et al. | 48/197 |
| 2008/0132588 A1 | 6/2008 | Pedersen et al. | |
| 2008/0142408 A1 | 6/2008 | Eilers et al. | 208/61 |
| 2008/0172941 A1 | 7/2008 | Jancker et al. | 48/73 |

FOREIGN PATENT DOCUMENTS

| | | |
|---|---|---|
| CH | 499614 A | 11/1970 |
| DE | 2624396 A | 12/1976 |
| DE | 2914806 A1 | 10/1979 |
| DE | 2949588 A1 | 6/1980 |
| DE | 3121991 A1 | 1/1983 |
| EP | 0045352 B1 | 10/1982 |
| EP | 0661373 | 7/1995 |
| EP | 0722999 | 7/1996 |
| EP | 1958921 A1 | 8/2008 |
| GB | 2018818 A | 10/1979 |
| WO | 9953561 | 10/1999 |
| WO | 0073404 A1 | 12/2000 |
| WO | 2007025691 A1 | 3/2007 |
| WO | WO2007125047 | 11/2007 |

OTHER PUBLICATIONS

Holm-Larsen, H. $CO_2$ reforming for large scale methanol plants—an actual case, Studies in Surface Science and Catalysis, vol. 136, pp. 441-446 (2001).
"Gasification" by Christopher Higman and Maarten van der Burgt, published by Elsevier (2003), especially chapters 4 and 5.
Xu, Jianguo et al., "Methane Steam Reforming, Methanation and Water-Gas Shift: I. Intrinsic Kinetics," AIChE Journal, Jan. 1989, vol. 35, No. 1, pp. 88-96.

*Primary Examiner* — Jafar Parsa (57) ABSTRACT

A process for the co-production of superheated steam and methane includes reacting a gas containing carbon monoxide and hydrogen in a series of methanation regions to produce a product gas containing methane The gas containing carbon monoxide and hydrogen flows, in passing through the series of methanation regions, successively through at least a first internally cooled methanation region and a second internally cooled methanation region, cooling the first and second internally cooled methanation region with water, which water is vaporized in the first internally cooled methanation region to produce steam and which steam is subsequently superheated in the second internally cooled methanation region to produce superheated steam The internally cooled methanation regions include tubes filled with a methanation catalyst and a space surrounding the tubes The gas containing carbon monoxide and hydrogen and/or product gas flows through the tubes and the water flows through the space surrounding the tubes.

11 Claims, 3 Drawing Sheets

PROCESS FOR THE CO-PRODUCTION OF SUPERHEATED STEAM AND METHANE

PRIORITY CLAIM

The present application claims priority from PCT/US2010/044065, filed 2 Aug. 2010, which claims priority from U.S. provisional application 61/230,777, filed 3 Aug. 2009.

TECHNICAL FIELD OF THE INVENTION

The invention relates to a process for the co-production of superheated steam and methane.

BACKGROUND OF THE INVENTION

A methanation reaction comprises a catalytic reaction of hydrogen with carbon monoxide to produce methane. This methane is sometimes also referred to as synthetic natural gas (SNG) and can be used as substitute gas for natural gas. In areas where there is little natural gas available, other sources of energy, such as coal or petroleum coke, may be partially oxidized in a gasification process to produce a gas comprising hydrogen and carbon monoxide. Such a gas comprising hydrogen and carbon monoxide is sometimes also referred to as synthesis gas. The synthesis gas can subsequently be used to produce synthetic natural gas (SNG) in a methanation process.

The methanation reaction proceeds, in the presence of a suitable methanation catalyst, in accordance with the following equations:

$$CO + 3H_2 = CH_4 + H_2O + \text{heat} \quad (1)$$

$$CO_2 + 4H_2 = CH_4 + 2H_2O + \text{heat} \quad (2).$$

The water formed during the reaction can, depending on the catalyst, temperature and concentrations present, subsequently react in-situ with carbon monoxide in a water-gas shift reaction in accordance with the following equation:

$$CO + H_2O = CO_2 + H_2 + \text{heat} \quad (3)$$

Reaction (1) is considered the main reaction and reactions (2) and (3) are considered to be side reactions. All the reactions are exothermic.

The methanation reactions are reversible and an increasing temperature will tend to shift the equilibrium towards a lower yield. To control the temperature, the methanation reaction can be carried out in one or more internally cooled reactors, where the reactants can be cooled by a coolant.

U.S. Pat. No. 4,839,391 describes a one-stage process for the methanation of synthesis gas to generate methane and superheated steam. The methanation reactor comprises a catalyst bed with different temperature regions, through which a cooling system passes. A cooling medium, i.e. water, flows through the cooling system countercurrently to the flow of synthesis gas through the catalyst bed. In the process, the synthesis gas successively flows through an inflow region, a hot spot region and an outward gas flow region. Cooling water is converted to steam by heat transfer in the outward gas flow region and hot spot region of the reactor, also referred to as vaporizer. Subsequently the steam is being superheated in the hot spot region of the reactor, also referred to as superheater. An external heat exchanger is used to preheat the water before entering the reactor against the effluent methane/synthesis gas mixture from the reactor.

In the embodiment of FIG. 2 of U.S. Pat. No. 4,839,391 a steam chamber is interposed between the vaporizer and the superheater. The steam flowing from the vaporizer collects in the steam chamber where still unvaporized cooling water carried along with the steam is separated. Collected dry steam is led to the superheater tube system and converted.

In the embodiment of FIG. 8 of U.S. Pat. No. 4,839,391 the vaporizer of the cooling system stretches over the entire length of a catalyst bed including the outward gas flow region, the hot spot region and the gas inflow region of a methanation reactor. A superheater is disposed in the hot spot region but projects into the outward gas flow region such that the superheater and vaporizer overlap for the full length of the superheater. A design is described that comprises steam superheating piping within catalyst tubes containing the catalyst, such that the reaction heat can be passed to both the coolant that is to be vaporized which surrounds the catalyst tubes and also to the vapor that is to be superheated.

The tube walls separating the superheated steam and the catalyst in the hot spot region need to be able to withstand high temperature and pressure. The temperature in the hot spot region and therefore the temperature of the tube walls separating the superheated steam and the catalyst may be more than 700° C. The tubes therefore require expensive construction material for its walls. In addition, the cooling system has a complex structure increasing the costs of the tube system even further.

In the embodiment of FIG. 6 of U.S. Pat. No. 4,839,391, the methanization reactor comprises a coolant vaporizer and a coolant superheater which form tube systems in the catalyst bed of the reactor. The reactor comprises a coolant preheater in the gas inflow region, a vaporizer exclusively located in the outward gas flow region of the methanation reactor and a hot spot region, which is cooled only by superheating steam. Although the reaction in the hot spot region is cooled by superheating the steam, the reaction temperature in the hot spot region is still very high. The temperature in the hot spot region and therefore the temperature of the reactor walls may be as high as 730° C. The reactor walls in the hot spot region therefore need to be able to withstand high temperature and pressure. In addition the reactor walls in the hot spot may require insulation. The hot spot region of the reactor therefore requires more expensive construction material for its walls than the other parts of the reactor.

U.S. Pat. No. 4,431,751 describes a method for producing superheated steam with the heat of catalytic methanation of a synthesis gas containing carbon monoxide, carbon dioxide and hydrogen. The process passes a gas stream first through a first internally water-cooled reactor, subsequently through an adiabatic reactor and a subsequent heat exchanger and finally through a second internally water-cooled reactor. The internally water-cooled reactors comprise a cooling system disposed within a catalyst bed through which water flows. As catalyst a nickel-containing catalyst is used. Water is passed in succession, first through the cooling system of the second internally water-cooled reactor for preheating thereof to a temperature approximating the saturated steam temperature, thereafter into the first internally water-cooled reactor for conversion into saturated steam and subsequently to the heat exchanger following the adiabatic reactor for superheating.

A disadvantage of the process of U.S. Pat. No. 4,431,751 is that a separate adiabatic reactor is needed to superheat the steam.

It would be an advancement in the art to provide a cheap and economic process for the co-production of superheated steam and methane. It would further be a special advancement in the art to provide a cheap and economic process, which would neither require any adiabatic reactors nor any expensive construction materials for superheating the steam.

SUMMARY OF THE INVENTION

The above has been achieved with the process according to the invention.

Accordingly, the present invention provides a process for the co-production of superheated steam and methane comprising reacting a gas containing carbon monoxide and hydrogen in a series of methanation regions to produce a product gas containing methane, wherein the gas containing carbon monoxide and hydrogen flows, in passing through the series of methanation regions, successively through at least a first internally cooled methanation region and a second internally cooled methanation region, cooling the first and second internally cooled methanation region with water, which water is vaporized in the first internally cooled methanation region to produce steam and which steam is subsequently superheated in the second internally cooled methanation region to produce superheated steam, wherein the internally cooled methanation regions comprise tubes filled with a methanation catalyst and a space surrounding the tubes; and wherein the gas containing carbon monoxide and hydrogen and/or product gas flows through the tubes and the water flows through the space surrounding the tubes.

The process according to the invention allows the co-production of methane and superheated steam without the necessity of adiabatic reactors, whilst the costs for the construction material of the methanation regions can be kept low. In the first internally cooled methanation region, the temperature of the tube walls can be similar to the temperature of the boiling water, which boiling water may have a temperature of for example around 300° C. In the second internally cooled methanation region, the temperature of the catalyst may already be lower than the temperature of the catalyst in the first internally cooled methanation region. The temperature of the tube walls in the second internally cooled methanation region can be similar to the temperature of the steam, which steam may have a temperature of for example around 450-500° C. The process of the invention has the advantage that the temperature of the metal of the tube walls can be reduced and that cheaper construction materials (for example cheaper metal) may be used in the methanation regions.

BRIEF DESCRIPTION OF THE DRAWINGS

The process according to the invention is illustrated with the following drawings.

DETAILED DESCRIPTION OF THE INVENTION

Without wishing to be bound to any kind of theory, it is believed that by cooling the first methanation region, where the temperature of the catalyst and feed may be highest, with water that is still to be vaporized, a more efficient cooling can be achieved. The water, that is still to be vaporized, is capable of absorbing more heat than steam that is being superheated. As a result the overall metal temperature in the first methanation region can be lower and less expensive material is needed for construction of the first methanation region. In the second methanation region, the temperature of the catalyst and feed may be lower and less cooling is required. The overall metal temperature in the second methanation region can avoid the use of special material for the tube walls.

The gas containing carbon monoxide and hydrogen, may be any gas comprising carbon monoxide and hydrogen. An example of a gas comprising carbon monoxide and hydrogen is synthesis gas. Herein synthesis gas is understood to be a gas comprising at least hydrogen and carbon monoxide. In addition, the synthesis gas may comprise other compounds such as carbon dioxide, water, nitrogen, argon and/or sulphur containing compounds. Examples of sulphur containing compounds that may be present in synthesis gas include hydrogen sulphide and carbonyl sulphide.

The synthesis gas may be obtained by reacting a carbonaceous feed and an oxidant in a gasification reaction.

By a carbonaceous feed is understood a feed comprising carbon in some form. The carbonaceous feed may be any carbonaceous feed known by the skilled person to be suitable for the generation of synthesis gas. The carbonaceous feed may comprise solids, liquids and/or gases. Examples include coal, such as lignite (brown coal), bituminous coal, sub-bituminous coal, anthracite, bitumen, oil shale, oil sands, heavy oils, peat, biomass, petroleum refining residues, such as petroleum coke, asphalt, vacuum residue, or combinations thereof. As the synthesis gas is used in a methanation process the synthesis gas is preferably obtained by gasification of a solid or liquid carbonaceous feed. In a preferred embodiment, the synthesis gas is obtained by gasification of a solid carbonaceous feed that comprises coal or petroleum coke.

By an oxidant is understood a compound capable of oxidizing another compound. The oxidant may be any compound known by the skilled person to be capable of oxidizing a carbonaceous feed. The oxidant may for example comprise oxygen, air, oxygen-enriched air, carbon dioxide (in a reaction to generate carbon monoxide) or mixtures thereof. If an oxygen-containing gas is used as oxidant, the oxygen-containing gas used may be pure oxygen, mixtures of oxygen and steam, mixtures of oxygen and carbon dioxide, mixtures of oxygen and air or mixtures of pure oxygen, air and steam.

In a special embodiment the oxidant is an oxygen-containing gas containing more than 80 vol %, more than 90 vol % or more than 99 vol % oxygen. Substantially pure oxygen is preferred. Such substantially pure oxygen may for example be prepared by an air separation unit (ASU).

In some gasification processes, a temperature moderator may also be introduced into the reactor. Suitable moderators include steam and carbon dioxide.

The synthesis gas may be generated by reacting the carbonaceous feed with the oxidant according to any method known in the art. In a preferred embodiment the synthesis gas is generated by a partial oxidation of a carbonaceous feed, such as coal or petroleum coke, with an oxygen-containing gas in a gasification reactor.

Synthesis gas leaving a gasification reactor is sometimes also referred to as raw synthesis gas. This raw synthesis gas may be cooled and cleaned in a number of subsequent cooling and cleaning steps. The total of the gasification reactor and the cooling and cleaning steps is sometimes also referred to as gasification unit.

Examples of suitable gasification processes, reactors for such gasification processes and gasification units are described in "Gasification" by Christopher Higman and Maarten van der Burgt, published by Elsevier (2003), especially chapters 4 and 5 respectively. Further examples of suitable gasification processes, reactors and units are described in US2006/0260191, WO2007125047, US20080172941, EP0722999, EP0661373, US20080142408, US20070011945, US20060260191 and U.S. Pat. No. 6,755,980.

Preferably raw synthesis gas produced by reacting a carbonaceous feed and an oxidant in a gasification process is cooled and cleaned before using it as a gas containing carbon monoxide and hydrogen in the process of the invention. The raw synthesis gas leaving a gasification reactor can for example be cooled by direct quenching with water or steam, direct quenching with recycled synthesis gas, heat exchangers or a combination of such cooling steps, to produce a cooled synthesis gas. In the heat exchangers, heat may be recovered. This heat may be used to generate steam or superheated steam. Slag and/or other molten solids that may be present in the produced synthesis gas can suitably be discharged from the lower end of a gasification reactor. Cooled synthesis gas can be subjected to a dry solids removal, such as a cyclone or a high-pressure high-temperature ceramic filter, and/or a wet scrubbing process, to produce a cleaned synthesis gas.

In a preferred embodiment, the gas containing carbon monoxide and hydrogen is desulphurized before using it in the process of the invention. The, preferably cooled and cleaned synthesis gas, may thus be desulphurized to produce a desulphurized synthesis gas, before it is used as gas containing carbon monoxide and hydrogen in the process of the invention. The desulphurization may be carried out in a desulphurizing unit, where sulphur containing compounds, such as hydrogen sulphide and carbonyl sulphide, can be removed from the gas containing carbon monoxide and hydrogen. Desulphurization can for example be carried out by so-called physical absorption and/or by a chemical solvent extraction process.

In addition the gas containing carbon monoxide and hydrogen may be treated to reduce the carbon dioxide content of the synthesis gas.

In one advantageous embodiment sulphur containing compounds and carbon dioxide in the gas containing carbon monoxide and hydrogen are removed in a combined sulphur/carbon dioxide removal unit.

In a further preferred embodiment the molar ratio of hydrogen to carbon monoxide in the gas containing carbon monoxide and hydrogen is increased before use of the gas in the process of the invention. The molar ratio of hydrogen to carbon monoxide in the gas can for example be increased by reacting carbon monoxide in the gas with water in a water-gas shift reaction. The water-gas shift reaction can be carried out before a desulfurization of the gas containing carbon monoxide and hydrogen, also referred to as a sour water-gas shift reaction, or after a desulfurization of the gas containing carbon monoxide and hydrogen, also referred to as a sweet water-gas shift reaction. Preferably a water-gas shift reaction is carried out before desulfurization of the gas containing carbon monoxide and hydrogen.

The water-gas shift reaction may comprise a so called high temperature water-gas shift reaction carried out at a temperature preferably above 250° C. and more preferably at a temperature in the range from 300 to 450° C. and/or a so called low temperature water-gas shift reaction, carried out at a temperature preferably below 250° C. and more preferably in the range from 150-225° C. In a preferred embodiment the molar ratio of hydrogen to carbon monoxide in the gas containing carbon monoxide and hydrogen is increased before desulfurization in a high temperature water-gas shift reaction.

The water-gas shift catalyst may be any catalyst known to be suitable for such purpose. The water-gas shift catalyst may for example contain copper, zinc, iron and/or chromium, optionally in the form of oxides and/or supported by a carrier. A high temperature water-gas shift reaction is preferably carried out using a catalyst containing iron and/or chromium. A low temperature water-gas shift reaction is preferably carried out using a catalyst containing copper and/or zinc oxide.

The shifted gas may comprise carbon monoxide, carbon dioxide, water and hydrogen. In addition, the shifted gas may comprise other compounds such as nitrogen and argon.

Water can be removed from the shifted gas by any method known to be suitable for that purpose. For example, water can be removed with a flash drum, knocking out preferably at least 70 wt % or more preferably at least 90 wt % of the water. Most preferably essentially all water is removed in the flash drum.

Carbon dioxide can be removed from the shifted gas in an acid gas removal unit. Carbon dioxide may be removed by any method known to be suitable for that purpose. For example carbon dioxide may be removed by cryogenic cooling, or by physical absorption or in a chemical solvent extraction process.

In an especially preferred embodiment a gas containing carbon monoxide and hydrogen, such as for example synthesis gas, is treated in a water-gas shift unit and subsequently sulfur-containing compounds, carbon dioxide and water are removed from it, before using it in the process of the invention.

In the process according to the invention at least part of the carbon monoxide and hydrogen in the gas containing carbon monoxide and hydrogen are reacted in a series of methanation regions to produce a product gas containing methane. The series of methanation regions comprises at least a first internally cooled methanation region and a second internally cooled methanation region. Preferably the series of methanation reactors further comprises at least a third successive internally cooled methanation region. The third successive internally cooled methanation region may advantageously be used to preheat water that is to be vaporized in the first internally cooled methanation region. When it is desired to prepare superheated steam with a high pressure, preferably 3 methanation regions are used.

The internally cooled methanation regions are cooled with water. By water is herein understood water in the liquid phase, in the vapour phase or in a mixture thereof. The water may for example be liquid water, steam or superheated steam.

The internally cooled methanation region(s) may each comprise a part of an internally cooled methanation reactor or each internally cooled methanation region may comprise one internally cooled methanation reactor. Preferably the first internally cooled methanation region consists of a first internally cooled methanation reactor and preferably the second internally cooled methanation region consists of a second internally cooled methanation reactor. If present, a third internally cooled methanation region preferably consists of a third internally cooled methanation reactor. The first and second internally cooled methanation region(s) may comprise (part of) any internally cooled reactor known in the art to be suitable for a methanation process. The internally cooled methanation region(s) may for example comprise a fixed bed comprising the methanation catalyst, which catalyst bed is cooled by a cooling system comprising one or more tubes through which the water flows. In another embodiment the internally cooled methanation region(s) may comprise one or more tubes containing the methanation catalyst, which tubes are cooled via a space surrounding the tubes through which water can flow.

Preferably the internally cooled methanation region(s) comprise tubes filled with a methanation catalyst through which the gas containing carbon monoxide and hydrogen flows and a space surrounding the tubes through which the water flows. By having the water flow through a space between the outside of the tubes and the inside of a (reactor) vessel instead of through the tubes, a more evenly distributed cooling can be achieved, avoiding hot-spots and/or cold-spots in the internally cooled methanation region. Also the heat control is improved as the distance across which the heat generated in the tubes needs to be transported is shorter than when a fixed bed or fluidized bed of catalyst is cooled by water flowing in a system of tubes. It further allows one to avoid high temperatures for the reactor walls.

The internally cooled methanation regions may be vertically oriented or horizontally oriented. Preferably the internally cooled methanation regions are vertically oriented. In such vertically oriented internally cooled regions the flow of the gas containing carbon monoxide and hydrogen may be bottom-up or top-down. Preferably the flow of the gas containing carbon monoxide and hydrogen is top-down.

In a further preferred embodiment the internally cooled methanation regions comprise one or more multitubular reactors. Such a multitubular reactor preferably comprises a substantially vertically extending vessel, a plurality of open-ended reactor tubes arranged in the vessel parallel to its central longitudinal axis, supply means for supplying the gas containing carbon monoxide and hydrogen to a top fluid chamber and an effluent outlet arranged in a bottom fluid chamber. Preferably the upper ends of the open-ended reactor tubes are fixed to an upper tube plate and in fluid communication with the top fluid chamber above the upper tube plate and the lower ends of the open-ended reactor tubes are fixed to a lower tube plate and in fluid communication with the bottom fluid chamber below the lower tube plate. The number of tubes in the multitubular reactor can vary within a wide range and also depends on the desired capacity. For practical purposes a number of tubes in the range from 10 to 20,000 is preferred and a number of tubes in the range of 100 to 10,000 is more preferred.

The internal diameter of the tubes should be small enough to allow a sufficient transfer of reaction heat to the water for cooling and large enough to avoid unnecessary material costs. The optimal diameter of the reactor tubes depends the amount of reactants and the catalyst used. In the process of the present invention reactor tube internal diameters in the range of 10 to 100 mm are preferred and reactor tube internal diameters in the range from 20 to 70 mm are more preferred.

The internally cooled methanation regions may comprise one or more methanation catalysts. The methanation catalyst may be any methanation catalyst known to be suitable for this purpose.

Preferably the methanation catalyst contains nickel and/or ruthenium. Most preferably the methanation catalyst is a nickel containing methanation catalyst. In addition to nickel such catalyst may optionally comprise molybdenum, cobalt and/or ruthenium. The methanation catalyst may comprise a carrier, which carrier may comprise for example alumina, silica, magnesium, zirconia or mixtures thereof. Preferably the catalyst is a nickel containing catalyst comprising in the range from 10 wt % to 60 wt % nickel and more preferably in the range from 10 wt % to 30 wt % nickel.

Any catalyst may be present in the internally cooled reactor in any form known to be suitable by the skilled person. The catalyst(s) may be present as a fixed bed or fluidized bed, the catalyst may be packed in a tubes present in the reactor, or the catalysts may be coated on granules packed in a reactor or coated on for example a tubular or spiral structure within the reactor.

Preferably the gas containing carbon monoxide and hydrogen is fed into the first internally cooled methanation region at a temperature in the range from 250° C. to 500° C., preferably in the range from 260° C. to 400° C., and more preferably in the range from 200 to 300° C. and a pressure in the range from 10 to 60 bar, preferably in the range from 20 to 50 bar, more preferably in the range from 25 to 45 bar. The flowrate of the gas mixture into one or more of the internally cooled methanation regions, on the basis of a plant producing 14.1 million standard cubic meters of methane-containing product gas per day, is preferably equal to or less than 150 Kmol/sec and preferably at least 10 Kmol/sec.

The gas containing carbon monoxide and hydrogen can flow through the internally cooled methanation regions in a direction cross-currently, co-currently or counter-currently to the stream of water. Preferably the gas containing carbon monoxide and hydrogen flows through the internally cooled methanation regions in a direction counter-currently to the direction in which the water flows through the internally cooled methanation regions.

If present, the water preferably enters a third internally cooled methanation region at a temperature in the range from 20-120° C. below the boiling temperature, preferably at a temperature in the range from 30-110° C. below its boiling temperature, and more preferably at a temperature in the range from 50-100° C. below its boiling temperature. Preferably the water enters any third internally cooled methanation region at a temperature below 275° C., more preferably at a temperature in the range from 200° C. to 270° C.

Alternatively water may be preheated in a heat exchanger using heat that is for example generated elsewhere in a gasification or methanation process.

Preheated water is preferably fed to the first internally cooled methanation region at a temperature in the range from 50° C. below boiling T up to boiling T and steam is obtained form the first internally cooled methanation region at boiling temperature. The steam is preferably superheated in the second internally cooled methanation region to a temperature in the range from 50 degrees above boiling point to about 200 ° C. above boiling point.

The water is preferably fed to the internally cooled methanation regions at a pressure in the range from 50 bar to 150 bar, preferably from 60 bar to 125 bar.

In a third internally cooled methanation region the water can be heated to a higher temperature. Preferably the water is heated in a third internally cooled methanation region to its boiling temperature. The water leaving a third internally cooled methanation region may be completely liquid or partly liquid, that is, the heated water may leave a third internally cooled methanation region as liquid or a liquid/vapour mixture. Preferably at least 50 wt %, more preferably at least 75 wt % and most preferably at least 90 wt % of the water leaving a third internally cooled methanation region leaves such region as a liquid. More preferably essentially all water leaving a third internally cooled methanation region is liquid.

Optionally the process according to the invention is carried out in a series of methanation regions, which series comprises the internally cooled methanation regions described above and one or more additional methanation region(s). The additional methanation region(s) may comprise one or more additional internally cooled methanation regions, one or more adiabatic methanation regions or a combination of internally cooled methanation region(s) and adiabatic methanation region(s). The additional methanation regions may contain the same or a different methanation catalyst than the above described internally cooled methanation region comprising the nickel containing methanation catalyst.

Preferably the series of methanation regions consists of the first internally cooled methanation region, the second internally cooled methanation region and optionally a third internally cooled methanation region.

Preferably all internally cooled methanation regions comprise tubes filled with a nickel comprising methanation catalyst and a space surrounding the tubes where the water flows through the space surrounding the tubes.

In a preferred embodiment the first internally cooled methanation region and/or the second or third internally cooled methanation region may contain a water-gas shift catalyst in addition to the methanation catalyst.

The water-gas shift catalyst may be any catalyst known to be suitable for such purpose as described above.

When present, the water-gas shift catalyst is preferably present as a mere separate layer of water-gas shift catalyst, located upstream of a methanation catalyst. When the water-gas shift catalyst is present upstream of the methanation catalyst, the gas containing carbon monoxide and hydrogen to the methanation region first passes the water-gas shift catalyst before coming into contact with the methanation catalyst.

The presence of such a water-gas shift catalyst is most advantageous in the first or most upstream methanation region. Without wishing to be bound by any kind of theory, it is believed that the water-gas shift catalyst advantageously allows water and carbon monoxide in the gas containing carbon monoxide and hydrogen to react thereby generating heat, which allows the gas containing carbon monoxide and hydrogen to increase quickly in temperature to a temperature high enough for the methanation reaction to initiate. For example, such a water-gas shift reaction may quickly increase the temperature of the (shifted) gas containing carbon monoxide and hydrogen to a temperature above 300° C. but below 400° C.

In a further preferred embodiment the first internally cooled methanation region and/or the second and/or third internally cooled methanation region may comprise an empty area not comprising any catalyst through which the gas containing carbon monoxide and hydrogen flows. For example the tubes in an internally cooled methanation region may comprise a first area, that comprises a catalyst, and a second area, upstream of the first area, that does not comprise any catalyst. The second area that does not comprise any catalyst can be used to preheat a flow of gas before it is contacted with the catalyst in the first area.

In addition to superheating the produced steam with heat generated in one or more of the other methanation regions, other sources of heat can be used to superheat the produced steam.

Preferably the steam produced in the first internally cooled methanation region is passed to a steam separation vessel before being superheated. As the water may contain dissolved mineral matter (for example iron, calcium or magnesium oxides) that could accumulate in the steam separation vessel, the steam separation vessel preferably comprises a bleed stream through which mineral matter can be removed. With the help of such a bleed stream the concentration of mineral matter can be kept below any level at which precipitation may occur. Such bleed stream can further be advantageous to control the liquid/vapour ratio in the steam separation vessel when this is desired.

For practical purposes, the bleed stream preferably comprises less than 1 wt % of the total water flow rate.

If it is necessary to add liquid water to the steam separation vessel, such liquid water may conveniently be obtained from flash-drums used to knock out water upstream or downstream of the methanation regions.

The produced superheated steam may be used for any purpose known by the person skilled in the art. For example the superheated steam may be used to generate power.

In a preferred embodiment at least part of the steam or superheated steam produced is added to the gas containing carbon monoxide and hydrogen to reduce coke formation in the internally cooled methanation regions.

In another preferred embodiment at least part of the steam or superheated steam produced is used in a gasification reaction to produce synthesis gas. The steam or superheated steam may for example be used as a temperature moderator in the gasification reaction, to generate power for the gasification reaction or to preheat the reactants for the gasification reaction.

The process according to the invention produces a product gas containing methane. In addition to methane the product gas may contain other compounds such as carbon dioxide, water, unreacted carbon monoxide, unreacted hydrogen, nitrogen and/or argon.

The product gas preferably has a temperature in the range from 250 to 350° C., more preferably a temperature in the range from 275 to 325° C. In a preferred embodiment the product gas is used to preheat the gas containing carbon monoxide and hydrogen and/or the cooling water. In such manner a most advantageous heat integration is obtained.

The product gas containing methane may subsequently be purified by any method known in the art to increase the methane content in the product gas. The, optionally purified, product gas containing methane can be used as a substitute for natural gas.

Figure 1:
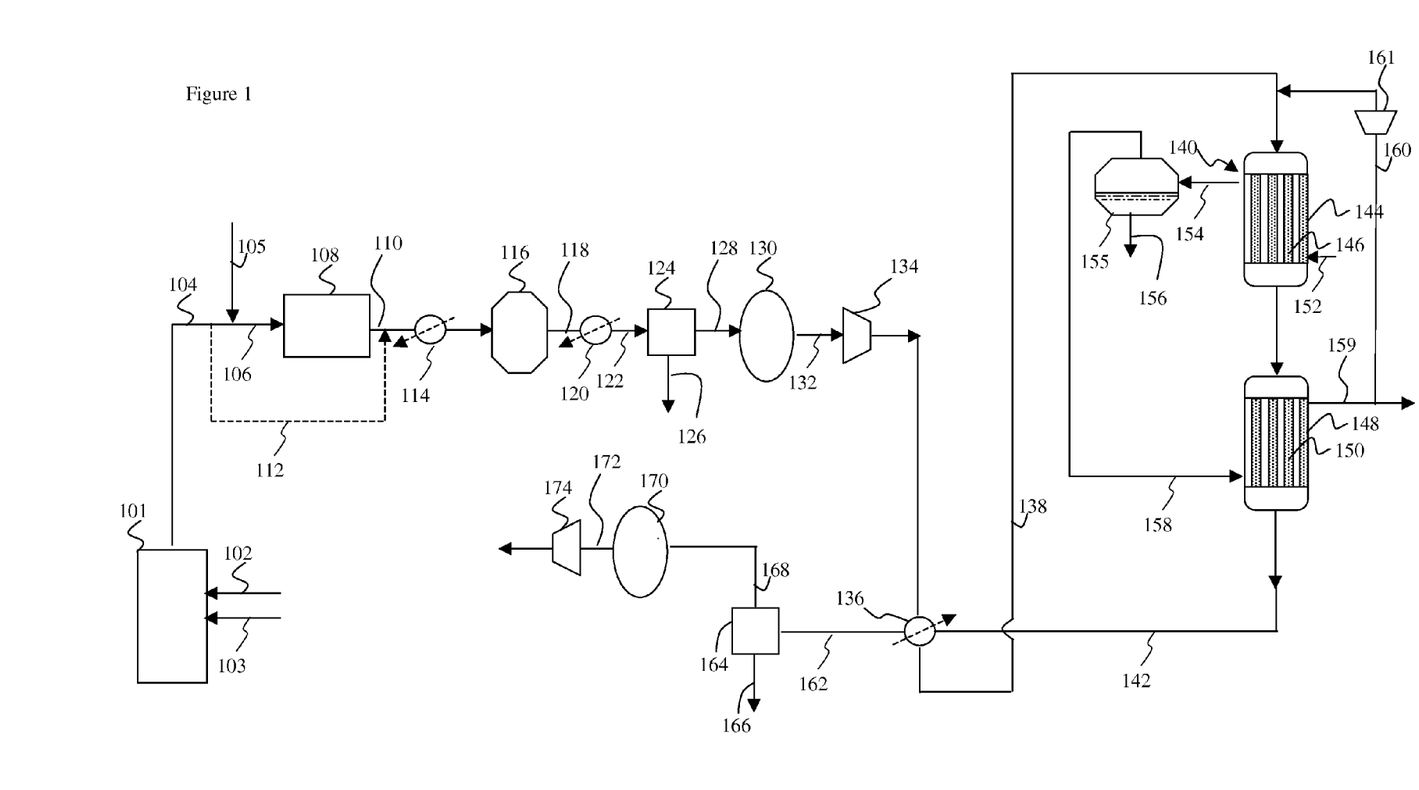
FIG. 1 schematically shows a first process according to the invention.

In FIG. 1, one example of a process according to the invention is shown. In a coal gasification unit (101) a stream of coal (102) is oxidized with an oxygen containing stream (103) to produce a synthesis gas stream (104). The synthesis gas stream (104) comprises carbon monoxide and hydrogen and may in addition optionally contain water and carbon dioxide. The synthesis gas stream (104) is combined with a steam stream (105) to provide a water gas shift feed stream (106). The water gas shift feed stream (106) is forwarded to a high temperature water-gas shift reactor (108) at a temperature of about 300-350° C. and leaves the high temperature water-gas shift reactor at a temperature of about 550° C. In the high temperature water-gas shift reactor, steam and the carbon monoxide react to produce a shifted synthesis gas stream (110), comprising a higher ratio of hydrogen to carbon monoxide. The shifted synthesis gas stream (110) may optionally be mixed with a stream of non-shifted synthesis gas (112).

Figure 3:
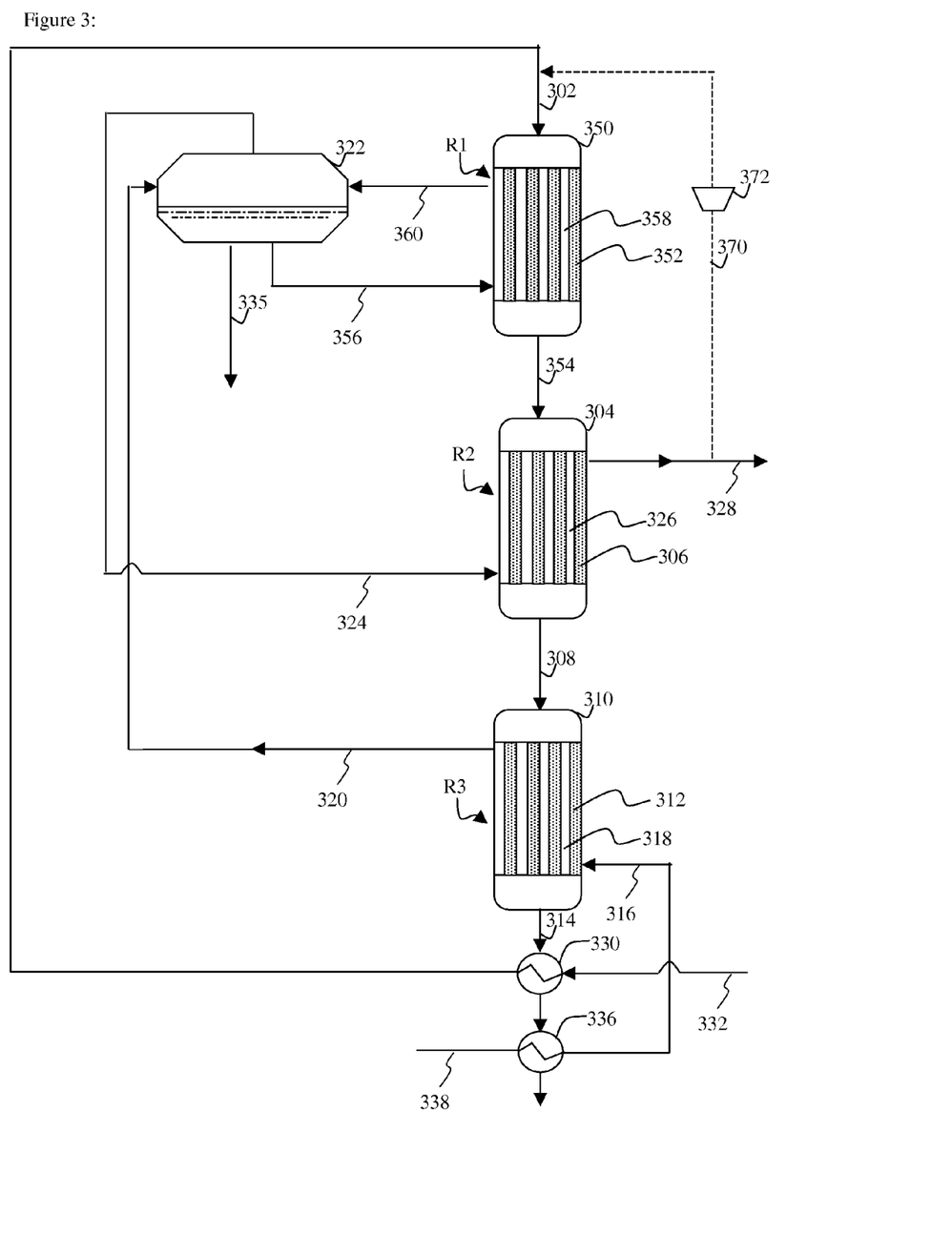
FIG. 3 schematically shows a third process according to the invention.

The shifted synthesis gas stream (110) is cooled in a heat exchanger (114) and subsequently desulphurized in a desulphurization unit (116) to produce a desulphurized synthesis gas stream (118). The desulphurized synthesis gas stream (118) is cooled down further in a heat exchanger (120), after which a cooled desulphurized synthesis gas stream (122) is forwarded to a flash drum (124) to remove water. In the flash drum (124) water is knocked out and removed via stream (126). The resultant stream (128) is forwarded to a carbon dioxide removal unit (130), where carbon dioxide is removed. The carbon dioxide removal unit (130) produces a stream (132) comprising a cooled and dried carbon dioxide-lean synthesis gas that can be used as a gas containing carbon monoxide and hydrogen for feeding to an internally cooled methanation region. The stream (132) of such gas containing carbon monoxide and hydrogen is compressed in compressor (134) and preheated in heat-exchanger (136) to produce a stream of gas containing carbon monoxide and hydrogen (138) with a temperature in the range from 270° C. and 300° C. and a pressure of about 35 bar. The stream of gas containing carbon monoxide and hydrogen (138) is forwarded to a series of methanation regions (140), comprising at least two internally cooled methanation regions. In the series of methanation regions a stream of product gas (142) containing methane is produced. In FIG. 1, a series of a first internally cooled methanation region (144) containing a methanation catalyst (146) and a second internally cooled methanation region (148) containing a methanation catalyst (150) is illustrated. As illustrated in FIG. 3 hereafter, however, the series of methanation regions can for example also comprise three internally cooled methanation regions containing a methanation catalyst.

The first internally cooled methanation region (144) and the second internally cooled methanation region (148) are cooled with water. A stream of liquid water (152) is heated in the first internally cooled methanation region (144) from a temperature of 232° C. at a pressure of 78 bar to its boiling temperature at 78 bar (i.e. 293° C.) to produce a stream comprising steam (154). The steam from stream (154) is collected in steam separation vessel (155) comprising a bleed stream (156). Subsequently a further stream comprising only steam (158) is withdrawn from the steam separation vessel (155) and superheated in the second internally cooled methanation region (148) to produce a stream comprising superheated steam (159). A stream (160) comprising part of the superheated steam may be split from the stream comprising superheated steam (159). This stream (160) may be used to generate power in an expander (161) and may subsequently be added to the stream of gas containing carbon monoxide and hydrogen (138) to avoid coking in the methanation region(s).

The stream of product gas (142) is cooled in heat exchanger (136) and a stream (162) of cooled product gas is forwarded to a flash drum (164) to remove water. In the flash drum (164) water is knocked out and removed via stream (166) and a stream (168) comprising cooled and dried product gas is produced. Stream (168) is forwarded to a carbon dioxide removal unit (170), where carbon dioxide is removed from the cooled and dried product gas. The carbon dioxide removal unit (170) produces a final product stream (172) comprising cooled and dried carbon dioxide-lean product gas that may be brought to a desired pressure in compressor (174).

Figure 2:
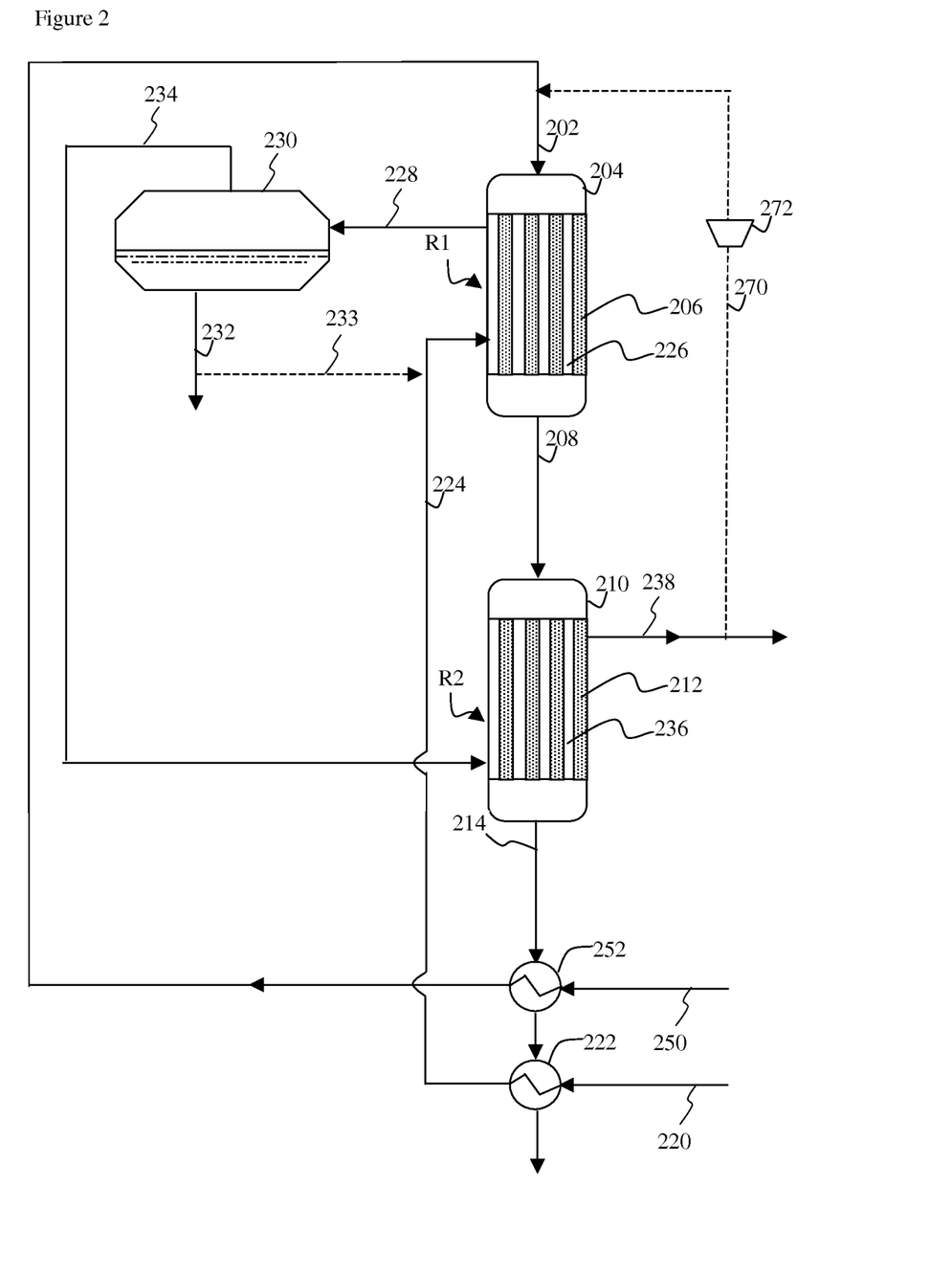
FIG. 2 schematically shows a second process according to the invention.

In FIG. 2, an example of a series of two internally cooled methanation regions that can be used in the process of the invention is illustrated. A stream of gas comprising carbon monoxide and hydrogen, having a temperature in the range from about 270 to about 300° C., enters a first internally cooled methanation region (204, R1 in the figure) comprising multiple tubes containing a nickel-based methanation catalyst (206) via line (202). In the first internally cooled methanation region (204) the carbon monoxide and hydrogen are partially converted and a stream of an intermediate product gas comprising methane and unreacted carbon monoxide and hydrogen, having a temperature of about 320° C., leaves the internally cooled methanation region (204) via a line (208) connecting the first internally cooled methanation region (204) with a second internally cooled methanation region (210, R2 in the figure). The intermediate product gas stream is fed into the second internally cooled methanation region (210) comprising multiple tubes containing a nickel-based methanation catalyst (212). In the second internally cooled methanation region (210) at least part of the remaining carbon monoxide and hydrogen react and a stream of a product gas comprising methane, having a temperature of about 300° C., leaves the second internally cooled methanation region (210) via a line (214).

The first internally cooled methanation region (204) and the second internally cooled methanation region (210) are cooled by a flow of water. A stream of water (220) is preheated in a heat exchanger (222). The water enters the first internally cooled methanation region (204) at the bottom via line (224) at a temperature of 293° C. and a pressure of 78 bar. The water cools the tubes (206) in the first internally cooled methanation region (204) by flowing through a space (226) surrounding the tubes (206). The water flows in such space (226) in a direction counter currently to the direction of the gas flow in the tubes (206). In the first internally cooled methanation region (204) the liquid water of 293° C. and pressure of 78 bar is converted to steam of 293° C. and 78 bar. Steam leaves the first internally cooled methanation region via a line (228) and flows into the steam separation vessel (230). The steam separation vessel (230) comprises a bleed stream (232). In addition, water may optionally be split off from bleed stream (232) and redirected via line (233) to line (224) entering the first internally cooled methanation region (204) to allow for a better flow control and to assist in controlling of the amount of liquid water in steam separation vessel (230).

Steam is withdrawn from the steam separation vessel (230) via line (234) and fed into the bottom of the second internally cooled methanation region (210) at a temperature of 293° C. and a pressure of 78 bar. The steam cools the tubes (212) in the second internally cooled methanation region (210) by flowing through the space (236) surrounding the tubes (212). The steam flows in such space (236) in a direction counter currently to the direction of the gas flow in the tubes (212). In the second internally cooled methanation region (210) the steam is superheated to a temperature of 450° C. at a pressure of 78 bar and leaves the second internally cooled methanation region (210) as superheated steam via line (238). A part of the superheated stream generated may be split off via line (270) and may be used to generate power in an expander (272) and/or may be added to the feed gas in line (202) to prevent coking in the methanation region(s).

In the embodiment of FIG. 2, the stream of product gas in line (214) is advantageously cooled in a heat exchanger (252) by a stream of feed gas (250) whilst this stream of feed gas (250) is simultaneously heated to a desired temperature for feeding via line (202) to the first internally cooled methanation region (204).

In FIG. 3, a third example of a process according to the invention is shown. The process of FIG. 3 is similar to that of FIG. 2, except that a third internally cooled methanation region (310, R3 in FIG. 3) has been positioned subsequent to the first cooled methanation region (350, R1 in FIG. 3) and the second cooled methanation region (304, R2 in FIG. 3). A stream of gas containing carbon monoxide and hydrogen (302) comprising carbon monoxide and hydrogen enters the first internally cooled methanation region (350) comprising multiple tubes containing a nickel-based methanation catalyst (352). In the first internally cooled methanation region (350) the carbon monoxide and hydrogen are partially converted in the region and a first stream (354) of a first intermediate product gas comprising methane and unreacted carbon monoxide and hydrogen leaves the first internally cooled methanation region (350) and is forwarded to the second internally cooled region (304) comprising multiple tubes containing a nickel-based methanation catalyst (306). In the second internally cooled methanation region (304) part of the remaining carbon monoxide and hydrogen in the first intermediate product gas react and a stream of a second intermediate product gas (308) comprising methane leaves the second internally cooled methanation region (304) and is forwarded to the third internally cooled methanation region (310) comprising multiple tubes containing a nickel-based methanation catalyst (312). In the third internally cooled methanation region (310) at least part of the remaining carbon monoxide and hydrogen react and a stream of a product gas comprising methane leaves the third internally cooled methanation region (310) via a line (314). The first internally cooled methanation region (350), the second internally cooled methanation region (304) and the third internally cooled methanation region (310) are cooled by a flow of water. In the embodiment shown in FIG. 3, the water enters the third internally cooled methanation region (310) at the bottom via line (316) at a temperature of 232° C. and a pressure of 78 bar, that is at a temperature 61° C. below the boiling temperature at that pressure (293° C.). The water cools the tubes (312) in the third internally cooled methanation region (310) by flowing through a space (318) surrounding the tubes (312). The water flows in such space (318) in a direction counter currently to the direction of the gas flow in the tubes (312). In the third internally cooled methanation region (310) the water is heated to its boiling temperature of 293° C. The water leaves the third internally cooled methanation region (310) from the top via line (320) as heated water in a mixed liquid/vapor phase. The heated water is passed to a steam separation vessel (322). Liquid water is withdrawn from the steam separation vessel (322) via a line (356) and fed into the bottom of the first internally cooled methanation region (350). The water cools the tubes (352) in the first internally cooled methanation region (350) by flowing through the space (358) surrounding the tubes (352). The water flows in such space (358) in a direction counter currently to the direction of the gas flow in the tubes (352). In the first internally cooled methanation region (350), the liquid water of 293° C. and pressure of 78 bar is partially converted to steam of 293° C. and 78 bar. Steam and water leave the first internally cooled methanation region (350) via a line (360) and flow back into the steam separation vessel (322).

Steam is withdrawn from the steam separation vessel (322) via line (324) and fed into the bottom of the second internally cooled methanation region (304) at a temperature of 293° C. and a pressure of 78 bar. The steam cools the tubes (306) in the second internally cooled methanation region (304) by flowing through the space (326) surrounding the tubes (306). The steam flows in such space (326) in a direction counter currently to the direction of the gas flow in the tubes (306). In the second internally cooled methanation region (304) the steam is superheated to a temperature of 450° C. at a pressure of 78 bar and leaves the first internally cooled reactor (304) as superheated steam via line (328). In the embodiment of FIG. 3, the stream of product gas in line (314) is advantageously cooled in a heat exchanger (330) by a stream of gas containing carbon monoxide and hydrogen of 40° C. (332) whilst this stream of gas containing carbon monoxide and hydrogen at 40° C. (332) is simultaneously heated to a desired temperature in the range from about 270° to about 300° C. for feeding via line (302) to the first internally cooled methanation region (350). In the embodiments of FIG. 3, the product gas in line (314) may advantageously be further cooled in a heat exchanger (336) by a stream of water at 40° C. (338) whilst this stream of water at 40° C. (338) is simultaneously heated to a desired temperature below 275° C. for feeding via line (316) to the third internally cooled methanation region (310).

Further a part of the superheated stream generated may be split off via line (370) and may be used to generate power in an expander (372) and/or may be added to the gas containing carbon monoxide and hydrogen in line (302) to prevent coking in the methanation regions or may be added elsewhere in the process.

The steam separation vessel (322) preferably comprises a bleed stream (335) to prevent any solid material in the water streams from accumulating in the steam separation vessel (322).

What is claimed is:

1. A process for the co-production of superheated steam and methane comprising:
    reacting a gas containing carbon monoxide and hydrogen in a series of methanation regions to produce a product gas containing methane, wherein the gas containing carbon monoxide and hydrogen flows, in passing through the series of methanation regions, successively through at least a first internally cooled methanation region and a second internally cooled methanation region;
    and cooling the first and second internally cooled methanation region with water, which water is vaporized in the first internally cooled methanation region to produce steam and which steam is subsequently superheated in the second internally cooled methanation region to produce superheated steam, wherein the internally cooled methanation regions comprise tubes filled with a methanation catalyst and a space surrounding the tubes; and wherein the gas containing carbon monoxide and hydrogen and/or product gas flows through the tubes and the water flows through the space surrounding the tubes.

2. The process according to claim 1, wherein the gas containing carbon monoxide and hydrogen and/or product gas flow through the internally cooled methanation regions in a direction counter-currently to the direction in which the water flows through the internally cooled methanation regions.

3. The process according to claim 1, wherein the series of methanation regions consists of a sequence of a first internally cooled methanation region, a second internally cooled methanation region and a third internally cooled methanation region.

4. The process according to claim 1, wherein the internally cooled methanation regions comprise a nickel containing methanation catalyst.

5. The process according to claim 1, further comprising storing steam produced in the first internally cooled methanation region in a steam separation vessel and retrieving the produced steam from the steam separation vessel to produce superheated steam in the second internally cooled methanation region.

6. The process according to claim 1, wherein at least part of the produced steam and/or at least part of the produced superheated steam is added to the gas containing carbon monoxide and hydrogen upstream of the first reactor.

7. The process according to claim 1, wherein at least part of the produced steam and/or at least part of the produced superheated strain is used as a moderator in a gasification reaction to produce synthesis gas.

8. The process according to claim 1, further comprising the use of the product gas containing methane as a substitute for natural gas.

9. The process according to claim 1, wherein the gas containing carbon monoxide and hydrogen is synthesis gas obtained by reacting a carbonaceous feed and an oxidant in a gasification reaction.

10. The process according to claim 9, wherein the carbonaceous feed comprises coal or petroleum coke.

11. The process according to claim 1, wherein the superheated steam is subsequently used to generate power.

* * * * *